United States Patent
Frances

(10) Patent No.: US 7,893,129 B2
(45) Date of Patent: *Feb. 22, 2011

(54) STABLE, CATIONICALLY POLYMERIZABLE/CROSSLINKABLE DENTAL COMPOSITIONS

(75) Inventor: Jean-Marc Frances, Meyzieu (FR)

(73) Assignee: Bluestar Silicones France SAS, Lyons (FR)

( * ) Notice: Subject to any disclaimer, the term of this patent is extended or adjusted under 35 U.S.C. 154(b) by 0 days.
This patent is subject to a terminal disclaimer.

(21) Appl. No.: 12/400,314

(22) Filed: Mar. 9, 2009

(65) Prior Publication Data
US 2009/0258961 A1    Oct. 15, 2009

Related U.S. Application Data

(63) Continuation of application No. 10/933,537, filed on Sep. 3, 2004, now abandoned, and a continuation of application No. PCT/FR03/02649, filed on Sep. 5, 2003.

(60) Provisional application No. 60/501,022, filed on Sep. 9, 2003.

(30) Foreign Application Priority Data

Jul. 12, 2002 (FR) .................................. 02 08857

(51) Int. Cl.
| | |
|---|---|
| A61K 6/087 | (2006.01) |
| A61F 2/01 | (2006.01) |
| C07D 303/02 | (2006.01) |
| C08G 59/20 | (2006.01) |
| C08G 59/68 | (2006.01) |
| C08F 2/50 | (2006.01) |
| G03F 7/029 | (2006.01) |
| A61L 27/34 | (2006.01) |
| A61C 5/00 | (2006.01) |

(52) U.S. Cl. .................. 523/113; 523/115; 522/25; 522/26; 522/27; 522/29; 522/31; 522/49; 522/53; 522/170; 522/908; 106/35; 433/228.1

(58) Field of Classification Search .............. 523/116, 523/113, 115; 433/228.1; 522/25, 26, 27, 522/29, 31, 49, 53, 170, 908; 106/35
See application file for complete search history.

(56) References Cited

U.S. PATENT DOCUMENTS 4,026,705 A    5/1977    Crivello et al.
(Continued)

FOREIGN PATENT DOCUMENTS

EP    0203829 A2    5/1986
(Continued)

OTHER PUBLICATIONS

Crivello, J. V.; Sasaki, H. Synthesis and Photopolymerization of Silicon-Containing Multifunctional Oxetane Monomers; Journal of Macromolecular Science, Part A, vol. 30, Issue 2 & 3, 1993, 173-187. Marcel Dekker, Inc.*

*Primary Examiner*—Mark Eashoo
*Assistant Examiner*—Michael Pepitone
(74) *Attorney, Agent, or Firm*—Buchanan, Ingersoll & Rooney, P.C.

(57) ABSTRACT

Stable, highly filled cationic dental compositions useful for the production of dental prostheses and dental restoration materials contain:

(1) at least one compound which is reactive cationically when activated, advantageously at least one UV- and cationically reactive oxirane-functionalized silicone;

(2) at least one dental filler, advantageously $SiO_2$;

(3) at least one organic polymer or copolymer dispersant having an amine index less than or equal to 100 mg of potassium hydroxide per gram of dispersant, advantageously a polyurethane/acrylate copolymer or alkylammonium salt thereof;

(4) at least one cationic photoinitiator, advantageously iodonium borate; and (5) optionally, at least one photosensitizer.

20 Claims, 1 Drawing Sheet

U.S. PATENT DOCUMENTS

| | | | |
|---|---|---|---|
| 4,032,673 A | 6/1977 | Schroeter et al. | |
| 4,069,056 A | 1/1978 | Crivello | |
| 4,136,102 A | 1/1979 | Crivello | |
| 4,138,255 A | 2/1979 | Crivello | |
| 4,147,552 A | 4/1979 | Specht et al. | |
| 4,173,476 A | 11/1979 | Smith | |
| 4,278,751 A | 7/1981 | Specht et al. | |
| 4,310,469 A | 1/1982 | Crivello | |
| 4,795,796 A | 1/1989 | Haubennestel et al. | |
| 4,939,069 A | 7/1990 | Kawabata et al. | |
| 4,973,722 A | 11/1990 | Doggweiler et al. | |
| 4,992,572 A | 2/1991 | Desobry et al. | |
| 5,047,376 A | 9/1991 | Baumann et al. | |
| 5,073,438 A | 12/1991 | Meier | |
| 5,340,898 A | 8/1994 | Cavezzan et al. | |
| 5,425,900 A | 6/1995 | Quednau | |
| 5,468,902 A | 11/1995 | Castellanos et al. | |
| 5,698,618 A * | 12/1997 | Kamikubo et al. | 524/88 |
| 5,877,232 A * | 3/1999 | Storch et al. | 523/116 |
| 5,882,393 A | 3/1999 | Quednau et al. | |
| 6,037,090 A | 3/2000 | Tanaka et al. | |
| 6,084,004 A * | 7/2000 | Weinmann et al. | 522/25 |
| 6,284,898 B1 * | 9/2001 | Moszner et al. | 549/214 |
| 6,306,926 B1 | 10/2001 | Bretscher et al. | |
| 6,310,115 B1 | 10/2001 | Vanmaele et al. | |
| 6,747,071 B1 | 6/2004 | Frances | |
| 7,235,602 B2 * | 6/2007 | Klettke et al. | 524/858 |
| 7,247,660 B2 * | 7/2007 | Frances | 523/113 |
| 2002/0035199 A1 * | 3/2002 | Breunig et al. | 524/588 |
| 2003/0225199 A1 * | 12/2003 | Breunig et al. | 524/588 |
| 2004/0171717 A1 * | 9/2004 | Frances | 523/115 |
| 2005/0119367 A1 * | 6/2005 | Dhaler et al. | 523/115 |

FOREIGN PATENT DOCUMENTS

| | | |
|---|---|---|
| EP | 0323584 A2 | 12/1988 |
| EP | 0354181 A2 | 7/1989 |
| EP | 0403197 B1 | 12/1990 |
| EP | 0562897 A1 | 3/1993 |
| EP | 0562922 A1 | 3/1993 |
| EP | 1050291 A2 | 4/2000 |
| FR | 2784025 A1 | 10/1998 |
| WO | WO 90/11303 | 10/1990 |
| WO | WO 98/07798 | 2/1998 |
| WO | WO 99/56864 A2 | 11/1999 |

* cited by examiner

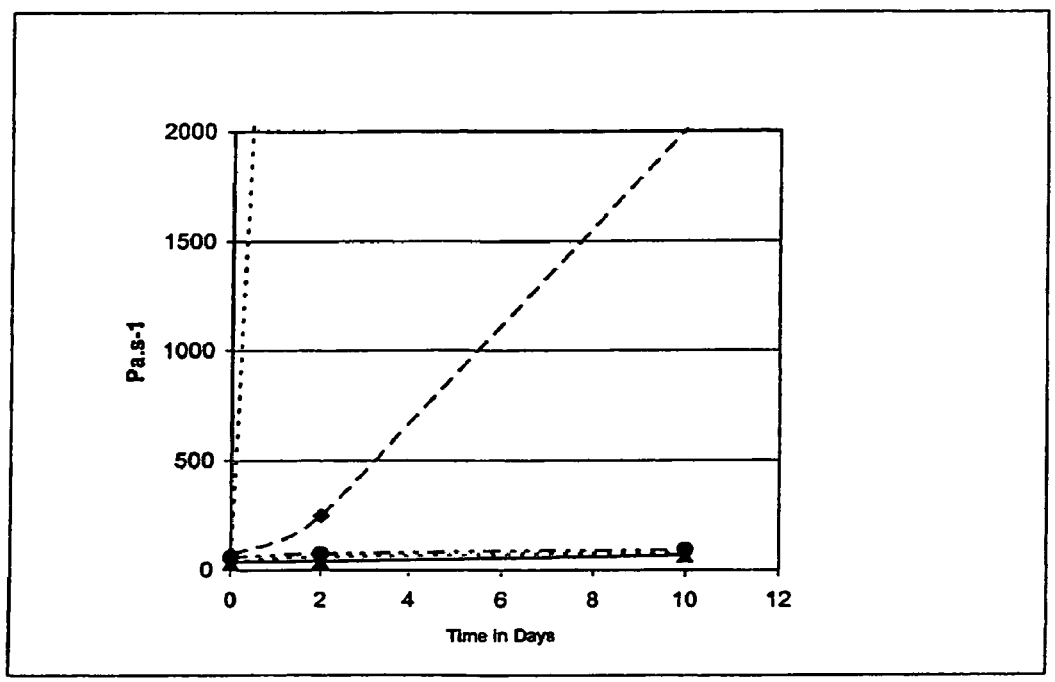

STABLE, CATIONICALLY POLYMERIZABLE/CROSSLINKABLE DENTAL COMPOSITIONS

CROSS-REFERENCE TO PRIORITY/PROVISIONAL APPLICATIONS

This application is a continuation application under 37 C.F.R. §1.53(b) of application Ser. No. 10/933,537, filed Sep. 3, 2004, which is now abandoned, and claims priority under 35 U.S.C. §119 of PCT/FR 03/02649, filed Sep. 5, 2003 and of provisional application Ser. No. 60/501,022, filed Sep. 9, 2003, each hereby expressly incorporated by reference in its entirety and each assigned to the assignee hereof. This application is also a continuation said PCT/FR 03/02649.

BACKGROUND OF THE INVENTION

1. Technical Field of the Invention

The present invention relates to dental compositions. More precisely, the dental compositions according to the present invention are useful for producing dental prostheses and for dental restoration.

2. Description of Background and/or Related and/or Prior Art

The conventional dental compositions are typically epoxy resins or photopolymerizable silicones or free-radically polymerizable acrylate resins. These compositions further include particulate reinforcing fillers (e.g., of hydrophobicized silica), photoinitiators and optionally photosensitizers in the case of cationic compositions or free-radical initiators for the free-radical compositions, and indeed other functional additives such as pigments or stabilizers.

After they have been mixed, these compositions are shaped and then photocrosslinked to a mass whose structure is like that of the teeth.

The fact that the filler is composed of very fine particles (≈0.05 μm) with a high specific surface area is a factor which limits its degree of incorporation into the resin. This is because the absorption capacity of the resin is limited. The result is that the filler levels of such compositions rarely reach more than 45% by volume.

This is therefore to the detriment of the mechanical reinforcement function assigned to the particulate filler.

This particulate filler may also interact with the reactive functions of the (photo)polymerizable/crosslinkable species and may therefore underlie problems of instability of the dental composition.

U.S. Pat. No. 6,306,926-B relates to dental compositions based on epoxy (e.g., polyTetraHydroFuran, UVR® 6105, EPON® 828, GY281®), oxetane or vinyl ether resins, among others, which are polymerizable/crosslinkable, cationically and under irradiation, and optionally (meth)acrylate resins which are polymerizable free-radically. In addition to the polymerization initiators, which are cationic photoinitiators and optionally free-radical initiators, as appropriate, these compositions comprise a microparticulate mineral filler which is radioopaque and is selected from the following metal compounds: oxides, halides, borates, phosphates, silicates, carbonates, germanates, tetrafluoroborates and hexafluorophosphates, having an isoelectric point of less than 7. This composition is such that its Barcol hardness is at least 10 after 30 minutes of cationic polymerization at 25° C.

These resins have the drawback of not being perfectly transparent to the actinic activating radiation of the UV-visible actinic polymerization, which is detrimental to the reaction kinetics and hence limits the possibilities of obtaining very thick photocrosslinked materials.

FR-A-2,784,025 is aimed at remedying this by proposing dental compositions based on silicone resins which are polymerizable/crosslinkable, cationically and under irradiation, with or without subsequent thermal post-crosslinking. These silicone resins contain oxirane (epoxide, oxetane, etc.) or vinyl ether functionalities, etc. Such compositions comprise one or more cationically polymerizable and/or crosslinkable polydimethylsiloxanes which carry on at least one of their ends reactive functions of formula:

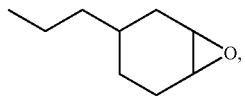

an effective amount of at least one onium borate initiator:

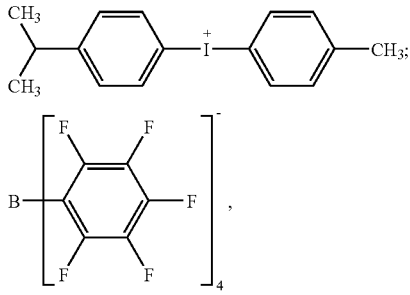

at least one photosensitizer, and an inert reinforcing or dental filler based on polymethyl methacrylate or on hexamethyldisilazane-treated fumed silica with a specific surface area of 200 m²/g, which is present in the composition in a proportion of at least 10% by weight relative to the total weight of the composition. These dental compositions are intended for the manufacture of prostheses or dental devices.

These silicones have the advantage over organic resins which crosslink cationically of being highly transparent to UV-visible light and hence of allowing very thick materials (several millimeters thick) to be obtained which are photocrosslinked within a very short time (less than one minute) with a UV lamp which emits in the visible field >400 nm.

These silicones, however, are formulated with reinforcing fillers that have Lewis or Brønsted acid character, such as quartzes or fumed silicas of very low particle size, whose surface silanols and/or residual water react with the cationic functions. Silicone formulations of this kind are therefore unstable on storage of the compositions.

Besides this problem of instability, brought about by the fillers, these silicone dental compositions remain capable of improvement in terms of increasing the degree of filling, optionally substituted so as to allow improvement in the mechanical properties.

Also known, through EP-A-1,050,291, are highly charged dental compositions which are presented as being endowed with good mechanical properties and contain from 10 to 70% by volume of filler (e.g., fumed silica) with a particle size Φm of 0.05-0.5 μm (less than 50% by volume of particles with a diameter Φ>0.50 μm), a free-radically photopolymerizable acrylic monomer and a phosphoric ester dispersant of formula:

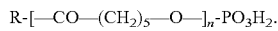

$$R-[-CO-(CH_2)_5-O-]_n-PO_3H_2.$$

Teaching of this kind relating to free-radical dental compositions can in no way be transposed to cationic dental compositions based on silicone. This is because the R-[—CO—$(CH_2)_5$—O—]$_n$-PO$_3$H$_2$ dispersants are not suitable for the cationic compositions, in particular since they contain a significant acid residue, RPO$_3$H$_2$, which reacts in the presence of oxirane functions and is detrimental to the stability of the composition.

It is therefore apparent that the prior art provides no satisfactory solution to the twin problem of stabilizing dental compositions based on units which are polymerizable cationically under UV (oxiranes, for example) and dispersing sizable amounts of fillers in the resin.

SUMMARY OF THE INVENTION

Novel dental compositions have now been developed which are based on structural units which are polymerizable cationically under UV (oxiranes, for example) that do not exhibit the drawbacks of the prior art in relation to stability and the limited degree of filling.

The present invention thus features novel cationic dental compositions, polymerizable and/or crosslinkable in an oral environment, which not only are stable and highly charged (e.g., ≧50%) but which also have markedly improved qualities, particularly as concerns the very clear reduction in the shrinkage phenomenon of dental compositions which are used for producing dental prostheses or dental restoration materials.

The present invention also features novel cationic dental compositions, polymerizable and/or crosslinkable in an oral environment, which not only are stable and highly charged (e.g., ≧50%) but which also have the advantage of being highly transparent to UV-visible light and hence of allowing very thick materials (several millimeters thick) to be obtained which are photocrosslinked within a very short time (less than one minute) with a UV lamp which emits in the visible field >400 nm.

This invention also features novel cationic dental compositions, polymerizable and/or crosslinkable in the oral environment, which not only are stable and highly charged (e.g., ≧50%) but which are also easy to prepare and economical.

Accordingly, the present invention first features dental compositions comprising:

(1) at least one compound which is reactive cationically and under activation, preferably actinic activation;

(2) at least one dental filler present in a proportion of at least 10% by weight relative to the total weight of the composition;

(3) at least one dispersant based on at least one organic polymer or copolymer selected from those whose amine index is less than or equal to 100 mg of potassium hydroxide per gram of dispersant;

(4) at least one cationic photoinitiator; and (5) optionally, at least one photosensitizer.

DETAILED DESCRIPTION OF BEST MODE AND SPECIFIC/PREFERRED EMBODIMENTS OF THE INVENTION

More particularly according to the present invention, it has now surprisingly and unexpectedly been shown that it is possible during formulation to use judiciously selected (co)polymer dispersants which allow the surface of the filler to be treated and thus allow the degree of filling to be increased and hence, ultimately, allow the material to be reinforced without detriment to the stability of the composite.

This stability translates to a useful life of a number of months or years.

These dispersants make it possible to fluidity the material without opacifying it, while retaining very substantial stability in the compositions. As a result of this attribute of the invention it is possible to use very high levels of treated filler of very low particle size, namely ≧50%.

This technical solution is all the more advantageous in being economically viable and easy to implement.

It is likewise of interest to observe that this composition provides satisfaction in terms of limiting the shrinkage after polymerization/crosslinking, which is entirely appreciable in dental application.

Generally speaking, photochemical activation is performed under UV radiation. More particularly, UV radiation with a wavelength of the order of from 200 to 500 nm is used for producing dental prostheses and UV-visible radiation with a wavelength of greater than 400 nm is used for producing restoration materials. A wavelength of greater than 400 nm allows crosslinking and/or polymerization in the oral environment.

Actinic (photochemical) activation may be advantageously complemented (or even replaced) by thermal activation.

The amine index of the dispersant (3) is preferably less than or equal to 60, and more preferably still between 0.1 and 50 mg of potassium hydroxide per gram of dispersant (3).

Advantageously the acid index of the dispersant is less than or equal to 200, preferably less than or equal to 100, and more preferably between 1 and 60 mg of potassium hydroxide per gram of dispersant.

According to one advantageous embodiment of the invention the dental filler (2) is present at from 10 to 85% by weight or by volume.

In accordance with the invention the dispersant (3) is advantageously selected from the group consisting of polyurethane/acrylate copolymers, optionally in alkylammonium salt form, acrylic copolymers, optionally in alkylammonium salt form, monoesters or diesters of carboxylic acids, polyesters, polyethers, polyurethanes, modified polyurethanes, polyol-polyacrylates, their copolymers or mixtures thereof.

The dispersants sold under the brand name Disperbyk® (from the company Byk) or Solsperse® (from the company Avecia) are particularly suitable for the invention.

In particular and by way of example, mention may be made of the following commercial products: Disperbyk® 164, Disperbyk® 161, Disperbyk® 166, Disperbyk® 2070, Disperbyk® 9075, Disperbyk® 9076.

U.S. Pat. No. 5,882,393-B describes dispersants based on polyurethanes/imidazole acrylates or epoxides.

U.S. Pat. No. 5,425,900-B describes dispersants based on polyurethanes. U.S. Pat. No. 4,795,796-B describes dispersants based on polyurethanes/polyoxyalkylene glycol monoalkyl ether.

WO-A-99/56864 describes dispersants based on polyurethanes/poly(oxyalkylene-carbonyl): derivatives of ε-caprolactone and of δ-valerolactone.

EP-B-0,403,197 describes grafted polyol-polyacrylate dispersants comprising a random polyurethane/polyvinyl/polyacrylate copolymer and a polyoxyalkylene polyether.

Quantitatively speaking, the dispersant (3) is present at from 50 ppm to 1%, preferably 100 ppm to 5000 ppm.

The cationically reactive compound (1) is preferably selected from the group of monomers and/or (co)polymers consisting of epoxies, vinyl ethers, oxetanes, spiroorthocarbonates, spiroorthoesters and combinations thereof.

More preferably still, the cationically reactive compound (1) is composed of at least one crosslinkable and/or polymerizable silicone oligomer or polymer which is liquid at ambient temperature or thermofusible at a temperature of less than 100° C. and comprises:

(1) at least one structural unit of formula (FS):

(FS)

in which $\underline{a}=0$, 1 or 2; the radicals $R^0$, which may be identical or different, are each an alkyl, cycloalkyl, aryl, vinyl, or alkoxy radical, or hydrogen, preferably a $C_1$-$C_6$ lower alkyl radical; and the radicals Z, which may be identical or different, are each an organic substituent containing at least one reactive epoxy and/or alkenyl ether and/or oxetane and/or dioxolane and/or carbonate functional group; and (2) at least two silicon atoms.

This silicone polymer or oligomer (1) has the advantage over organic resins which crosslink cationically of being transparent to UV-visible light, and hence its use allows very thick materials to be obtained whose photocrosslinking takes place within a short time.

The reactive functions Z of the silicone polymer or oligomer (1) may be very varied. Particularly advantageous dental compositions are obtained, however, when the silicone oligomer or polymer (1) comprises at least one unit (FS) in which Z represents an organic substituent Z1 containing at least one reactive epoxy and/or dioxolane function, and preferably at least one reactive epoxy function.

According to two advantageous embodiments of the present invention, the silicone oligomer or polymer (1) with at least one reactive epoxy and/or dioxolane function Z1 and preferably at least one reactive epoxy function may:

(i) either contain solely this (these) type(s) of reactive function(s) Z1;

(ii) or contain other reactive functions Z such as reactive alkenyl ether, oxetane and/or carbonate functions Z2.

In the case of the first embodiment (i) the dental composition may also comprise other silicone oligomers and/or polymers containing other reactive functions Z2 such as alkenyl ether, oxetane and/or carbonate functions and optionally reactive functions Z1.

As examples of reactive functions Z, these functions may in particular be selected from among the following radicals:

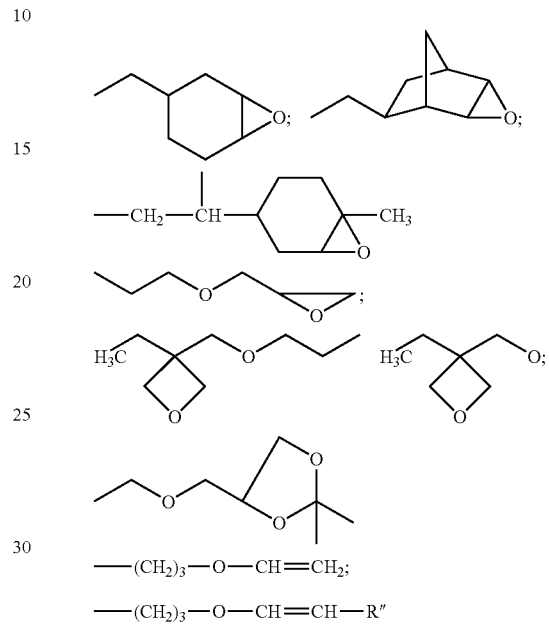

with R" representing a linear or branched $C_1$-$C_6$ alkyl radical.

According to a second advantageous embodiment of the present invention, the silicone polymer or oligomer is composed of at least one silicone having the following average formula:

a)
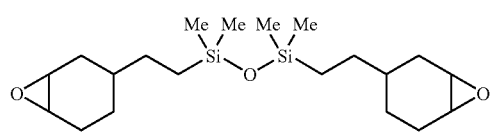

b)
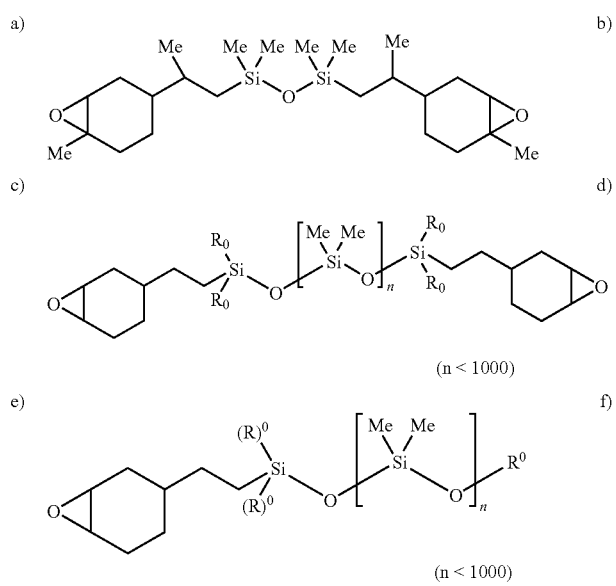

c)
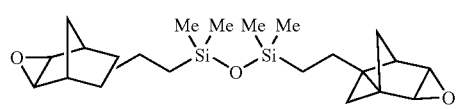

e)
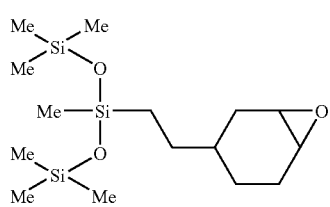

-continued
g)
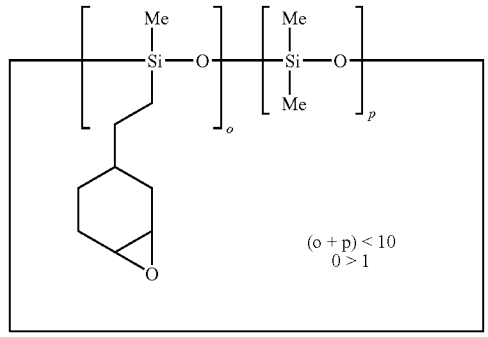
h)
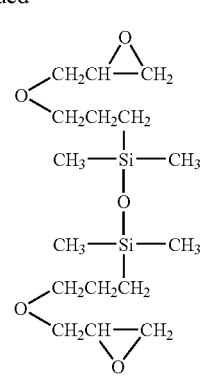
i)
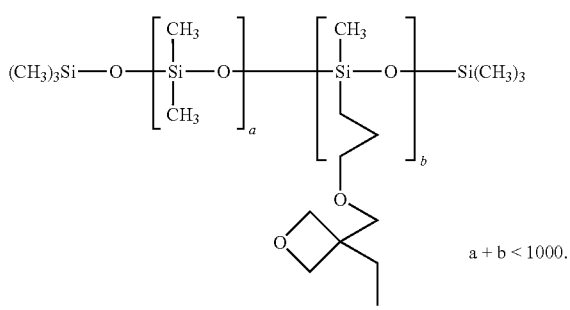
$a + b < 1000.$
j)
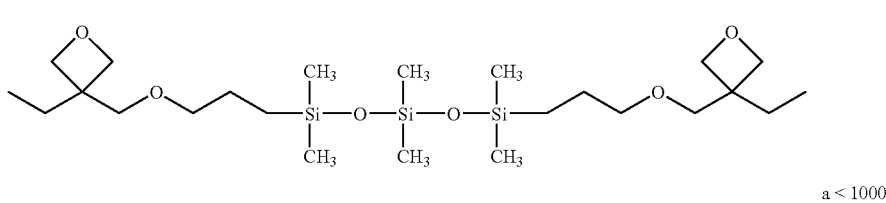
$a < 1000$
k)
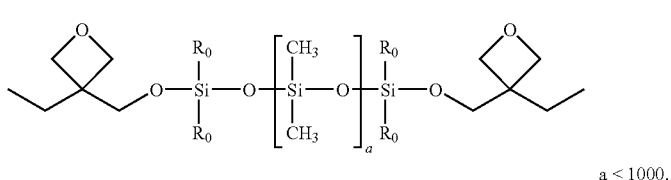
$a < 1000.$
l)
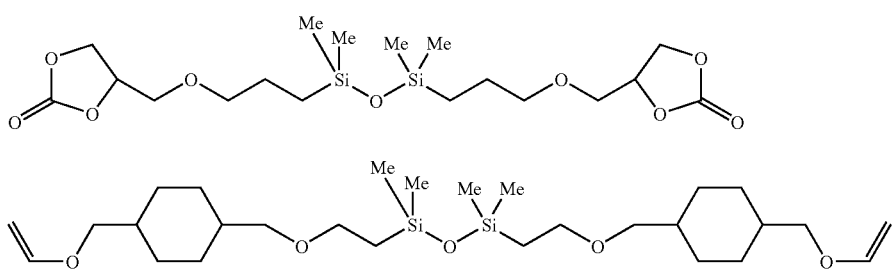
m)

-continued n)

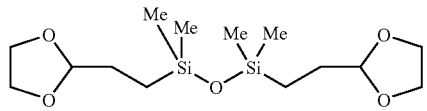

o)

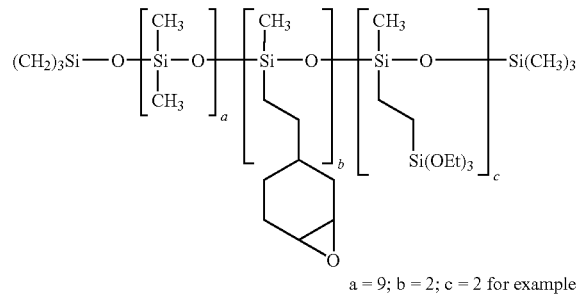

a = 9; b = 2; c = 2 for example

Different types of fillers (2) can be used for preparing the compositions according to the invention. The fillers are selected as a function of the end use of the dental composition: they affect important properties such as the appearance, the penetration of UV radiation and the mechanical and physical properties of the material obtained after crosslinking and/or polymerization of the dental composition.

As reinforcing filler use may be made of treated or untreated pyrogenic silica fillers, amorphous silica fillers, quartz, glasses or non-vitreous fillers based on zirconium oxide, barium oxide, calcium oxide, fluorine oxide, aluminum oxide, titanium oxide, zinc oxide, borosilicates, aluminosilicates, talc, Spherosil, ytterbium trifluoride, fillers based on polymers in ground powder form, such as inert or functionalized polymethyl methacrylates, and polyepoxies or polycarbonates.

By way of example mention may be made of:

inert, polymethyl methacrylate-based Luxaself fillers from the company UGL, which can be used in the dental field and are pigmented pink;

hexamethyidisilazane-treated fumed silica fillers with a specific surface area of 200 m²/g;

untreated fumed silica fillers (Aerosil AE200, sold by Degussa);

quartzes or silicon oxide glasses.

According to one advantageous embodiment of the invention, the fillers, and in particular the silica fillers, are treated before use at 120° C. with an amount less than 10% w/w of silicone containing at least one unit of the formula (XXIII):

 (XXIII)

such that Z' has the same definition as Z; $\underline{a}$=0, 1, 2; and with at least one silicon atom.

The cationic photoinitiators are selected from onium borates (taken by themselves or as a mixture between one another) of an element from Groups 15 to 17 of the Periodic Table [Chem. & Eng. News, vol. 63, No. 5, 26 of 4 Feb. 1985] or of an organometallic complex of an element from Groups 4 to 10 of the Periodic Table [same reference].

The borate cationic entity is selected from:

(1) onium salts of formula (I):

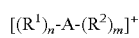 (I)

in which formula:

A represents an element from Groups 15 to 17 such as, for example, I, S, Se, P or N;

$R^1$ represents a $C_6$-$C_{20}$ heterocyclic or carbocyclic aryl radical, with the proviso that said heterocyclic radical may contain nitrogen or sulfur as heteroelements;

$R^2$ represents $R^1$ or a $C_1$-$C_{30}$ linear or branched alkyl or alkenyl radical, the said radicals $R^1$ and $R^2$ being optionally substituted by a $C_1$-$C_{25}$ alkoxy, $C_1$-$C_{25}$ alkyl, nitro, chloro, bromo, cyano, carboxyl, ester or mercapto group;

$\underline{n}$ is an integer ranging from 1 to v+1, $\underline{v}$ being the valency of the element A; and $\underline{m}$ is an integer ranging from 0 to v−1 with $\underline{n}$+$\underline{m}$=$\underline{v}$+1;

(2) the oxoisothiochromanium salts described in WO 90/11303, particularly the sulfonium salt of 2-ethyl-4-oxisothiochromanium or of 2-dodecyl-4-oxoisothiochromanium;

(3) organometallic salts of formula (III):

$$(L^1L^2L^3M)^{+q} \quad (III)$$

in which formula:

M represents a metal from Groups 4 to 10, especially iron, manganese, chromium or cobalt;

$L^1$ represents 1 ligand attached to the metal M by π electrons, the ligand being selected from $\eta^3$-alkyl, $\eta^5$-cyclopentadienyl and $\eta^7$-cycloheptatrienyl ligands and $\eta^6$-aromatic compounds selected from optionally substituted $\eta^6$-benzene ligands and compounds having 2 to 4 fused rings, each ring being capable of contributing to the valence shell of the metal M by 3 to 8π electrons;

$L^2$ represents one ligand attached to the metal M by π electrons, the ligand being selected from $\eta^7$-cycloheptatrienyl ligands and $\eta^6$-aromatic compounds selected from optionally substituted $\eta^6$-benzene ligands and compounds having 2 to 4 fused rings, each ring being capable of contributing to the valence shell of the metal M by 6 or 7π electrons;

$L^3$ represents from 0 to 3 identical or different ligands attached to the metal M by a electrons and selected from CO and $NO_2^+$, the total electronic charge q of the complex to which $L^1$, $L^2$ and $L^3$ contribute and the ionic charge of the metal M being positive and equal to 1 or 2.

The formula of the anionic borate entity is $[BX_aR_b]^-$, in which:

<u>a</u> and <u>b</u> are integers ranging from 0 to 3 for <u>a</u> and from 1 to 4 for <u>b</u>, with <u>a</u>+<u>b</u>=4, the symbols X represent:

a halogen atom (chlorine, fluorine) with <u>a</u>=0 to 3, or an OH function with <u>a</u>=0 to 2;

the symbols R, which may be identical or different, are each:

a phenyl radical substituted by at least one electron-withdrawing group such as, for example, $OCF_3$, $CF_3$, $NO_2$ or CN and/or by at least 2 halogen atoms (especially fluorine), when the cationic entity is an onium of an element from Groups 15 to 17;

a phenyl radical substituted by at least one electron-withdrawing element or group, particularly halogen atom (especially fluorine), $CF_3$, $OCF_3$, $NO_2$ or CN, when the cationic entity is an organometallic complex of an element from Groups 4 to 10;

an aryl radical containing at least two aromatic nuclei such as, for example, biphenyl, naphthyl, optionally substituted by at least one electron-withdrawing element or group, particularly a halogen atom (especially fluorine), $OCF_3$, $CF_3$, $NO_2$ or CN, irrespective of the cationic entity.

Although not limitative, the text below contains a number of further details regarding the subclasses of onium borate and of organometallic salt borate which are more particularly preferred in accordance with the invention.

According to a first preferred embodiment of the invention, the species of the anionic borate entity which are especially suitable are as follows:

1': $[B(C_6F_5)_4]^-$
2': $[(C_6F_5)_2BF_2]^-$
3': $[B(C_6H_4CF_3)_4]^-$
4': $[B(C_6F_4OCF_3)_4]^-$.
5': $[B(C_6H_3(CF_3)_2)_4]^-$
6': $[B(C_6H_3F_2)_4]^-$
7' $[C_6F_5BF_3]^-$

According to a second preferred embodiment of the invention, the onium salts (1) which can be used are described in numerous documents, particularly in U.S. Pat. Nos. 4,026,705-A, 4,032,673-A, 4,069,056-A, 4,136,102-A and 4,173,476-A. Among these salts, very particular preference will be given to the following cations:

$[(\Phi)_2I]^+$; $[C_8H_{17}—O-\Phi-I-\Phi]^+$; $[CH_3-\Phi-I-\Phi-CH_2CH(CH_3)_2]^+$; $[C_{12}H_{25}-\Phi-I-\Phi]^+$; $[(C_8H_{17}—O-\Phi)_2I]^+$; $[(C_8H_{17}—O-\Phi-I-\Phi)]^+$; $[(\Phi)_3S]^+$; $[(\Phi)_2-S-\Phi-O—C_8H_{17}]^+$; $[(CH_3-\Phi-I-\Phi-CH(CH_3)_2]^+$; $[\Phi-S-\Phi-S-(\Phi)_2]^+$; $[(C_{12}H_{25}-\Phi)_2I]^+$; $[(CH_3-\Phi-I-\Phi-OC_2H_5]^+$; $[(C_{12}H_{25}-\Phi-I-\Phi-CH—(CH_3)_2]^+$.

According to a third preferred embodiment, the organometallic salts (4) which can be used are described in U.S. Pat. Nos. 4,973,722-A, 4,992,572-A, EP-A-203,829, EP-A-323,584 and EP-A-354,181. The organometallic salts most desirable according to the invention are in particular:

($\eta^5$-cyclopentadienyl)($\eta^6$-toluene)Fe$^+$,
($\eta^5$-cyclopentadienyl)($\eta^6$-methyl-1-naphthalene)Fe$^+$,
($\eta^5$-cyclopentadienyl)($\eta^6$-cumene)Fe$^+$,
bis($\eta^6$-mesitylene)Fe$^+$,
bis($\eta^6$-benzene)Cr$^+$.

In accordance with these three preferred embodiments, mention may be made, as examples of onium borate photoinitiators, of the following products:

$[(C_8H_{17})—O-\phi-I-\phi]^+,[B(C_6F_5)_4]^-$;
$[C_{12}H_{25}-\phi-I\phi]^+,[B(C_6F_5)_4]^-$;
$[(C_8H_{17})—O-\phi)_2I]^+,[B(C_6F_5)_4]^-$;
$[(C_8H_{17})—O-\phi-I-\phi)]^+,[B(C_6F_5)_4]^-$;
$[(\phi)_2S-\phi-O—C_8H_{17}]^+,[B(C_6H_4CF_3)_4]^-$;
$[(C_{12}H_{25}-\phi)_2I]^+,[B(C_6F_5)_4]^-$;
$[CH_3-\phi-I-\phi-CH(CH_3)_2]^+,[B(C_6F_5)_4]^-$;
($\eta^5$-cyclopentadienyl)($\eta^6$-toluene)Fe$^+$,$[B(C_6F_5)_4]^-$;
($\eta^5$-cyclopentadienyl)($\eta^5$-methyl-1-naphthalene)Fe$^+$,$[B(C_6F_5)_4]^-$;
($\eta^5$-cyclopentadienyl)($\eta^6$-cumene)Fe$^+$,$[B(C_6F_5)_4]^-$;
$[(C_{12}H_{25}-\phi)_2I]^+,[B(C_6H_3(CF_3)_2)]^-$;
$[CH_3-\phi-I-\phi-CH_2CH(CH_3)_2]^+,[B(C_6F_5)_4]^-$;
$[CH_3-\phi-I-\phi-CH_2CH(CH_3)_2]^+,[B(C_6H_3(CF_3)_2)_4]^-$.

As another literature reference for defining the onium borates (1) and (2) and the organometallic salt borates (4), mention may be made of the entirety of the content of EP 0 562 897 and 0 562 922.

As another example of onium salts which can be used as a photoinitiator, mention may be made of those disclosed in U.S. Pat. Nos. 4,138,255 and 4,310,469.

It is also possible to use other cationic photoinitiators, e.g.,: iodonium hexafluorophosphate or hexafluoroantimonate salts, such as:

—$[CH_3-\phi-I-\phi-CH(CH_3)_2]^+,[PF_6]^-$;
—$[CH3-\phi-I-\phi-CH_2CH(CH_3)_2]^+, [PF_6]^-$;
—$[C_{12}H_{25}-\phi)_2-I]^+,[PF_6]^-$;
or the ferrocenium salts of these various anions.

The photosensitizer present within the dental composition according to the invention may be very varied in nature. According to the invention, it corresponds in particular to one of the following formulae (IV) to (XXII):

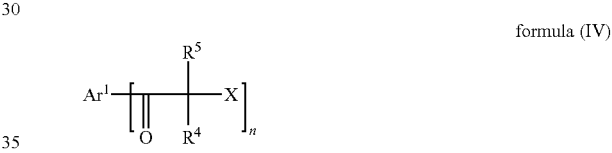

formula (IV)

in which:

when $\underline{n}$=1, $Ar^1$ represents an aryl radical containing 6 to 18 carbon atoms, a tetrahydronaphthyl, thienyl, pyridyl or furyl radical or a phenyl radical which carries one or more substituents selected from the group consisting of F, Cl, Br, CN, OH, linear or branched $C_1$-$C_{12}$ alkyls, —$CF^3$, —$OR^6$, —Ophenyl, —$SR^6$, —Sphenyl, —$SO_2$phenyl, —$COOR^6$, —O—($CH_2$—CH=$CH_2$), —O($CH_2H_4$—O)$_m$—H, —O($C_3H_6O$)$_m$—H, $\underline{m}$ ranging from 1 to 100;

when $\underline{n}$=2, $Ar^1$ represents a $C_6$-$C_{12}$ arylene radical or a phenylene-T-phenylene radical in which T represents —O—, —S—, —$SO_2$— or —$CH_2$—;

X represents a group —$OR^7$ or —$OSiR^8(R^9)_2$ or together with $R^4$ forms a group —O—$CH(R^{10})$—;

$R_4$ represents a linear or branched $C_1$-$C_8$ alkyl radical which is unsubstituted or carries an OH, —$OR^6$, $C_2$-$C_8$ acyloxy, —$CF_3$ or —CN group, a $C_3$ or $C_4$ alkenyl radical, a $C_6$-$C_{18}$ aryl radical or a $C_7$ to $C_9$ phenylalkyl radical;

$R^5$ has one of the meanings given for $R^4$ or represents a radical —$CH_2CH_2R^{11}$, or else together with $R^4$ forms a $C_2$-$C_8$ alkylene radical or a $C_3$-$C_9$ oxaalkylene or azaalkylene radical;

$R^6$ represents a lower alkyl radical containing 1 to 12 carbon atoms;

$R^7$ represents a hydrogen atom, a $C_1$-$C_{12}$ alkyl radical, a $C_2$-$C_6$ alkyl radical which carries an —OH, —$OR^6$ or CN group, a $C_3$-$C_6$ alkenyl radical, a cyclohexyl or benzyl radical, a phenyl radical optionally substituted by a chlorine atom or a linear or branched $C_1$-$C_{12}$ alkyl radical or a 2-tetrahydropyranyl radical;

$R^8$ and $R^9$, which may be identical or different, each represent a $C_1$-$C_4$ alkyl radical or a phenyl radical;

$R^{10}$ represents a hydrogen atom, a $C_1$-$C_8$ alkyl radical or a phenyl radical;

$R^{11}$ represents a radical —$CONH_2$, —$CONHR^6$, —$CON(R^6)_2$, —$P(O)(OR^6)_2$ or 2-pyridyl;

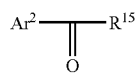

formula (V)

in which:

$Ar^2$ has the same meaning as $Ar^1$ in the formula (IV) in the case where $\underline{n}$=1;

$R^{15}$ represents a radical selected from the group consisting of a radical $Ar^2$, a linear or branched $C_1$-$C_{12}$ alkyl radical, a $C_6$-$C_{12}$ cycloalkyl radical and a cycloalkyl radical forming a $C_6$-$C_{12}$ ring with the carbon of the ketone or a carbon of the radical $Ar^2$, with the proviso that these radicals may be substituted by one or more substituents selected from the group consisting of —F, —Cl, —Br, —CN, —OH, —$CF_3$, —$OR^6$, —$SR^6$, —$COOR^6$, linear or branched $C_1$-$C_{12}$ alkyl radicals which optionally carry an —OH, —$OR^6$ and/or —CN group, and linear or branched $C_1$-$C_8$ alkenyl radicals;

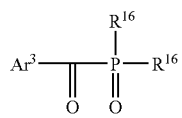

formula (VI)

in which:

$Ar^3$ has the same meaning as $Ar^1$ in the formula (IV) in the case where $\underline{n}$=1;

$R^{16}$, which may be identical or different, each represents a radical selected from the group consisting of a radical $Ar^3$, a radical —(C=O)—$Ar^3$, a linear or branched $C_1$-$C_{12}$ alkyl radical, a $C_6$-$C_{12}$ cycloalkyl radical, with the proviso that these radicals may be substituted by one or more substituents selected from the group consisting of —F, —Cl, —Br, —CN, —OH, —$CF_3$, —$OR^6$, —$SR^6$, —$COOR^6$, linear or branched $C_1$-$C_{12}$ alkyl radicals which optionally carry an —OH, —$OR^6$ and/or —CN group, and linear or branched $C_1$-$C_8$ alkenyl radicals;

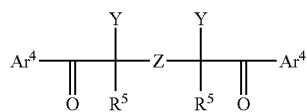

formula (VII)

in which the radicals $R^5$, which may be identical or different, have the same meaning as in formula (III);

the radicals Y, which may be identical or different, are each X and/or $R^4$;

Z represents:

a direct bond, a divalent $C_1$-$C_6$ alkylene radical, or a phenylene, diphenylene or phenylene-T-phenylene radical (T: linear or branched $C_1$-$C_{12}$ alkyl), or else forms, together with the two substituents $R^5$ and the two carbon atoms which carry these substituents, a cyclopentane or cyclohexane nucleus, a divalent group —O—$R^{12}$—O—, —O—$SiR^8R^9$—O—$SiR^8R^9$—O—, or —O—$SiR^8R^9$—O—, wherein $R^{12}$ represents a $C_2$-$C_8$ alkylene, a $C_4$-$C_6$ alkenylene or xylylene radical, or else the entity:

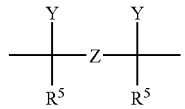

corresponds to —O—O; and $Ar^4$ has the same meaning as $Ar^1$ in the formula (IV) in the case where $\underline{n}$=1;

class of the thioxanthones of formula (VIII):

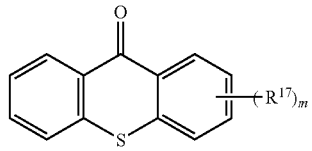

$\underline{m}$=0 to 8, $R^{17}$, identical or different substituent(s) on the aromatic ring(s), represent a linear or branched $C_1$-$C_{12}$ alkyl radical, a $C_6$-$C_{12}$ cycloalkyl radical, a radical $Ar^1$, a halogen atom or an —OH, —CN, —$NO_2$ or —$COOR^6$ group;

CHO, —Ophenyl, —$CF_3$, —$SR^6$, —Sphenyl, —$SO_2$phenyl, —Oalkenyl or —$SiR^6_3$;

class of the xanthenes of formula (IX):

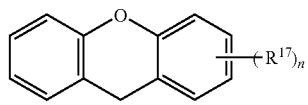

$\underline{n}$=0 to 8;

class of the xanthones of formula (X):

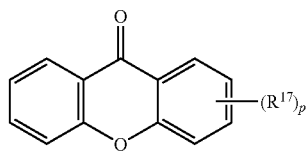

$\underline{p}$=0 to 8;

class of the naphthalene of formula (XI):

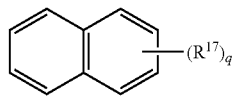

q=0 to 8;
class of the anthracene of formula (XII):

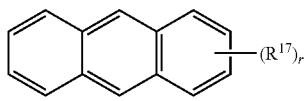

r=0 to 10;
class of the phenanthrene of formula (XIII):

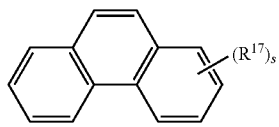

s=0 to 10;
class of the pyrene of formula (XIV):

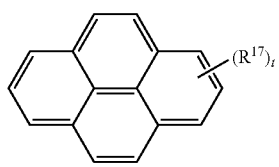

t=0 to 10;
class of the fluorene of formula (XV):

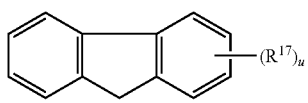

u=0 to 9;
class of fluoranthene of formula (XVI):

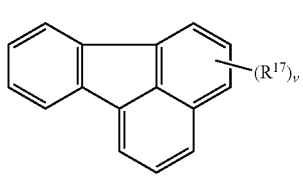

v=0 to 10;
class of the chrysene of formula (XVII):

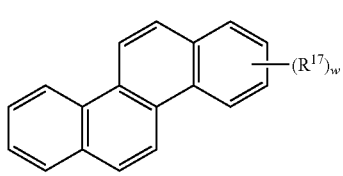

w=0 to 12;
class of the fluorene of formula (XVIII):

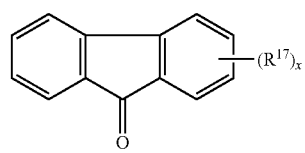

with x=0 to 8, for example 2,7-dinitro-9-fluorenone;
class of the chromone of formula (XIX):

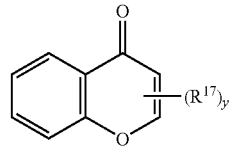

with y=0 to 6;
class of the eosine of formula (XX):

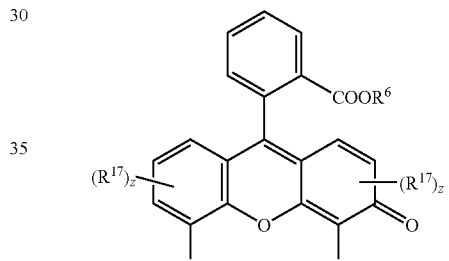

with z=0 to 5 with z=0 to 6;
class of the erythrosine of formula (XXI):

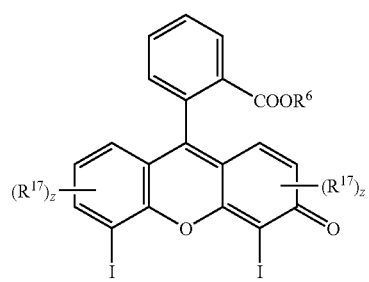

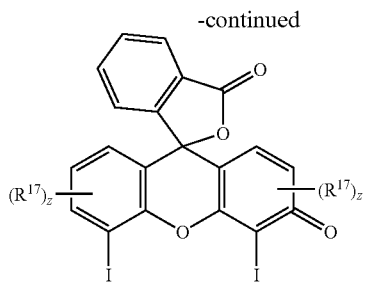

with z=0 to 5 with z=0 to 6;

class of the biscoumarins of formula (XXII):

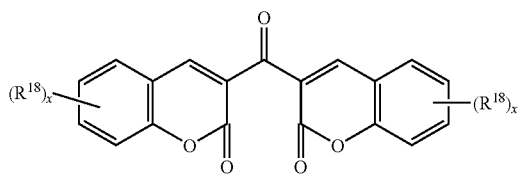

wherein the radicals $R^{18}$, which may be identical or different, each has the same meaning as $R^{17}$ or represents a group $-NR^6_2$; for example, 3,3'-carbonylbis (7-diethylaminocoumarin) and 3,3'-carbonylbis(7-methoxycoumarin).

Other sensitizers can be used. In particular, it is possible to use the photosensitizers described in U.S. Pat. Nos. 4,939,069, 4,278,751 and 4,147,552.

According to the present invention, the photosensitizers have a residual absorption of UV light between 200 and 500 nm, preferably 400 to 500 nm for the dental prostheses preparations. For dental restoration preference will be given to a photosensitizer having a residual absorption of UV light above 400 nm.

According to one preferred embodiment, the photosensitizers will be selected from those of classes (IV), (VI), (VII) and (VIII). By way of examples, mention may be made of the following photosensitizers:

4,4'-dimethoxybenzoin;
2,4-diethylthioxanthone;
2-ethylanthraquinone;
2-methylanthraquinone;
1,8-dihydroxyanthraquinone;
dibenzoyl peroxide;
2,2-dimethoxy-2-phenylacetophenone; benzoin;
2-hydroxy-2-methylpropiophenone; benzaldehyde;
4-(2-hydroxyethoxy)phenyl 2-hydroxy-2-methylpropyl ketone;
benzoylacetone;

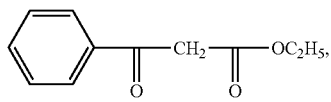

2-isopropylthioxanthone;
1-chloro-4-propoxythioxanthone;
4-isopropylthioxanthone;

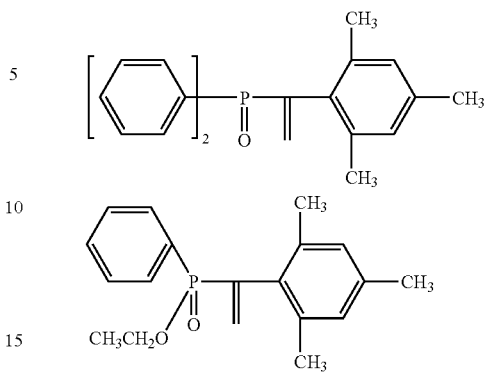

and mixtures thereof.

Where a siliceous filler or fillers, in particular silica, is or are treated with this type of polymer, the material obtained after crosslinking exhibits a markedly improved mechanical strength, elasticity modulus and compressive strength.

In addition to the reinforcing fillers, pigments may be used in order to color the dental composition in accordance with the intended use and the ethnic groups.

For example, red pigments are used in the presence of microfibers for the dental compositions used for preparing dental prostheses in order to simulate blood vessels.

Use is also made of pigments based on metal oxides (iron oxides and/or titanium oxide and/or aluminum oxide and/or zirconium oxide, etc.) for dental compositions used for preparing restoration material, so as to give an ivory-colored crosslinked material.

Other additives may be incorporated within the dental compositions according to the invention. Examples include biocides, stabilizers, flavors, plasticizers and adhesion promoters.

Among the additives that may be considered, use will be made advantageously of organic coreactants which are crosslinkable and/or polymerizable. These coreactants are liquid at ambient temperature or thermofusible at a temperature less than 100° C., and each coreactant comprises at least two reactive functions such as oxetane-alkoxy, oxetane-hydroxyl, oxetane-alkoxysilyl, carboxyl-oxetane, oxetane-oxetane, alkenyl ether-hydroxyl, alkenyl ether-alkoxysilyl, epoxy-alkoxy, epoxy-alkoxysilyl, dioxolane-dioxolane-alcohol, etc.

The dental compositions according to the invention may be used for numerous dental applications, and in particular in the field of dental prostheses, in the field of dental restoration and in the field of temporary teeth.

The dental compositions according to the invention are preferably in the form of a single product comprising the various components ("monocomponent"), thereby facilitating its employment, particularly in the field of dental prostheses. If appropriate the stability of this product may be ensured by means of amine-functional organic derivatives in accordance with the teaching of WO 98/07798.

In the field of dental prostheses, the product in the "monocomponent" form may be deposited with the aid of a syringe directly on the plaster model or in a core. It is then polymerized (polymerization by possible successive layers) with the aid of a UV lamp (visible light spectrum 200-500 nm).

In general it is possible to produce an aesthetic and durable dental prosthesis in 10 to 15 minutes.

It should be noted that the products obtained from the dental composition according to the invention are non-porous. Hence, after optional polishing with the aid of a felt brush, for example, the surface of the dental prostheses obtained is smooth and bright and therefore does not require the use of varnish.

The applications in the field of dental prostheses are essentially those of the attached prosthesis, which can be divided into two types:

total prosthesis in the case of a patient with no teeth at all partial prosthesis owing to the absence of several teeth, resulting either in a temporary prosthesis or in a skeleton brace.

In the field of dental restoration, the dental composition according to the invention may be used as material for filling the anterior and posterior teeth in different colors (for example, "VITA" colors), and is rapid and easy to use.

Since the dental composition is non-toxic and can be polymerized in thick layers, it is not essential to polymerize the material in successive layers. In general a single injection of the dental composition is sufficient.

The preparations for dental prostheses and for restoration materials are carried out according to the usual techniques of the art.

In the case of application of the dental composition to a tooth, either the tooth may be pretreated with a bonding primer or else the dental composition may be prepared as a mixture with a bonding primer prior to its use.

BRIEF DESCRIPTION OF THE DRAWING

The single FIGURE of drawing attached represents the curves of change in viscosity in Pa·s$^{-1}$ as a function of the storage period in days. The legend of this FIGURE is as follows:

---◆--- control 1
---•--- control 2
-▲- inventive formulation 1 (example 2.2)
------- inventive formulation 2 (example 2.3)
- - •---- inventive formulation 3 (example 2.4)

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLES AND TESTS

The silicone (1) containing epoxide functionality Z and used in the examples is (A):

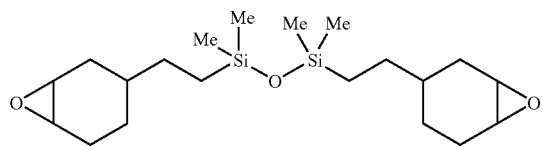

(A)

It is obtained from 4-vinycyclohexene epoxide (VCMX), sold by Union Carbide® (systematically distilled prior to use), and from tetramethyl-hydrodisiloxane (M'$_2$), used and manufactured by Rhodia Silicones, which is also distilled prior to use, in the presence of moist Pt on black catalyst 2S, sold by Aldrich under the reference 33,015-9. The platinum content is 1.2% by weight. The degree of moisture is 50% by weight.

The functionalization auxiliary used is sodium hydrogencarbonate (NaHCO$_3$).

The common operating protocol is as follows:

A 100 ml reactor is charged with 66 g (531 mmol=1.05 eq) of VCMX, the required amount of platinum in the form of the Pt on black catalyst 2S, and optionally water and sodium hydrogencarbonate. The reaction mixture is subsequently heated to 90° C. 34 g (506 mmol=1 eq) of M'$_2$ are then run dropwise into the reactor over 5 h. In the course of the synthesis the progress of the reaction is determined by the disappearance of the ≡SiH units and the disappearance where appropriate of the epoxy functions, which is monitored by potentiometric assay. When all of the ≡SiH units have undergone reaction, the reaction mixture is filtered and then devolatilized for 7 hours under vacuum at a high temperature in the presence or absence of sodium hydrogencarbonate. The viscosity, which is directly correlated with the loss of epoxide functions, is measured before and after devolatilization.

The product obtained contains between 85 and 99% of silicone (1) of formula (A) above and of CAS RN 18724.32.-8.

The onium borate photoinitiator (3) used to initiate the polymerization of the epoxy groups under UV is described in EP-0-562,897.

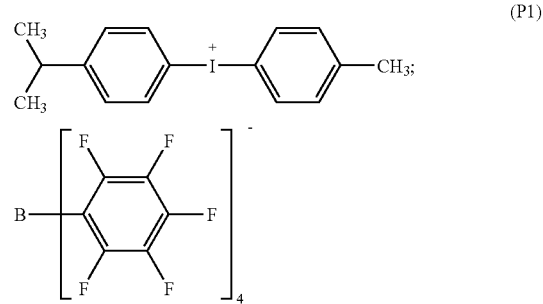

(P1)

The filler (2) used is a quartz which is sold by Schott under the reference G018-066 with particle sizes of 0.7 µm; 1.5 µm; 3.5 µm; or 5 µm.

These quartzes are analyzed in infrared by diffuse reflection and three zones of silanol bands are recorded (free silanols; associated silanols 1; and associated silanols 2) between 3300-4000 cm$^{-1}$. The concentration of active silanol sites increases with the available surface area and increases as the particle size is reduced.

Example 1

1.1 Preparation of a Control Formulation 1 without Dispersant

A Hauschild® centrifuge mixer is charged with 25 g of quartz (SiO$_2$>99%) with a particle size of 5 µm, sold by Schott, 3 g of ytterbium trifluoride, 10 g of siloxane resin having a monomer (A) content >90%, obtained by hydrosilylating VCMX according to a preparation process as described above.

Stirring is carried out for 16 s with the centrifuge mixer and then 1.25 g of photoinitiator system are added, containing 30% of photoinitiator P1 and 0.23% of a photosensitizer based on chloropropoxythioxanthone CPTX, sold by Lambson, all in solution in the resin (A) without solvent. Stirring is carried out for 16 s with the centrifuge mixer. Then 5 g of fumed silica ($SiO_2$>99%) are added and the mixture is stirred for 16 s. 5.75 g of fumed silica are added and the mixture is then stirred for 16 s.

The fumed silica is a silica sold by Degussa under the name OX-50, with a specific surface area of 40 $m^2$/g.

The curve of change in viscosity is given in the single FIGURE attached.

The preparation is gelled after 1 month when stored at 20° C.

1.2 Preparation of a Control Formulation 2 without Dispersant

A Hauschild® centrifuge mixer is charged with 25 g of quartz ($SiO_2$>99%) with a particle size of 3 μm, sold by Schott, 3 g of ytterbium trifluoride, 10 g of siloxane resin having a monomer (A) content >90%, obtained by hydrosilylating VCMX, as described above.

Stirring is carried out for 16 s with the centrifuge mixer and then 1.25 g of photoinitiator system in (A) are added, containing 30% of photoinitiator P1 and 0.23% of a photosensitizer (4) based on chloropropoxythioxanthone CPTX, sold by Lambson. Stirring is carried out for 16 s with the centrifuge mixer. Then 5 g of fumed silica ($SiO_2$>99%) are added and the mixture is stirred for 16 s. 5.75 g of fumed silica are added and the mixture is then stirred for 16 s. The fumed silica is a silica sold by Degussa under the name OX-50, with a specific surface area of 40 $m^2$/g.

The curve of change in viscosity is given in the single FIGURE attached.

The preparation is gelled after 48 hours when stored at 20° C.

Example 2

2.1. Preparation According to the Invention

The dispersant Byk® 164 (8 g) is dissolved in the resin (A) at 4% and the solution is subsequently devolatilized so as to remove the butyl acetate present in the dispersant, by heating under a vacuum of 10 mmHg at 60° C. for 3 hours in a rotary evaporator.

The active substance concentration is 2.4%.

2.2 Preparation of a Formulation 1 with Dispersant

A Hauschild® centrifuge mixer is charged with 25 g of quartz ($SiO_2$>99%) with a particle size of 5 μm, sold by Schott, 3 g of ytterbium trifluoride, 1.25 g of the solution of dispersant Byk® 164 devolatilized in the resin (A) as described above, and stirring is carried out for 16 s with the centrifuge mixer. 9 g of resin (A) are added.

Stirring is carried out for 16 s with the centrifuge mixer and then 1.25 g of photoinitiator system in (A) are added, containing 30% of photoinitiator P1 and 0.23% of photosensitizer CPTX. Stirring is carried out for 16 s with the centrifuge mixer. Then 5 g of fumed silica ($SiO_2$>99%) are added and the mixture is stirred for 16 s. 5.5 g of fumed silica are added and the mixture is then stirred for 16 s.

The change in viscosity is monitored over time.

The preparation does not gel after 1 month when stored at 20° C.

The curve of change in viscosity is given in the single FIGURE attached.

2.3 Preparation of a Formulation 2 with Dispersant

A Hauschild® centrifuge mixer is charged with 25 g of quartz ($SiO_2$>99%) with a particle size of 3 μm, sold by Schott, 3 g of ytterbium trifluoride, 1.25 g of the solution of dispersant Byk® 164 devolatilized in the resin (A), and stirring is carried out for 16 s with the centrifuge mixer. 9 g of resin (A) are added.

Stirring is carried out for 16 s with the centrifuge mixer and then 1.25 g of photoinitiator system in (A) are added, containing 30% of photoinitiator P1 and 0.23% of photosensitizer CPTX. Stirring is carried out for 16 s with the centrifuge mixer. Then 5 g of fumed silica ($SiO_2$>99%) are added and the mixture is stirred for 16 s. 5.5 g of fumed silica are added and the mixture is then stirred for 16 s.

The change in viscosity is monitored over time.

The preparation does not gel after 1 month when stored at 20° C.

The curve of change in viscosity is given in the single FIGURE attached.

2.4 Preparation of a Formulation 3 with Dispersant

A Hauschild® centrifuge mixer is charged with 25 g of quartz ($SiO_2$>99%) with a particle size of 1.5 μm, sold by Schott, 3 g of ytterbium trifluoride, 1.25 g of the solution of dispersant Byk® 164 devolatilized in the resin (A), and stirring is carried out for 16 s with the centrifuge mixer. 9 g of resin (A) are added.

Stirring is carried out for 16 s with the centrifuge mixer and then 1.25 g of photoinitiator system in (A) are added, containing 30% of photoinitiator P1 and 0.23% of a photosensitizer based on chloropropoxythioxanthone CPTX. Stirring is carried out for 16 s with the centrifuge mixer.

Then 5 g of fumed silica ($SiO_2$>99%) are added and the mixture is stirred for 16 s.

5.5 g of fumed silica are added and the mixture is then stirred for 16 s.

The change in viscosity is monitored over time.

The preparation does not gel after 1 month when stored at 20° C.

The curve of change in viscosity is given in the single FIGURE attached.

The viscosity is measured by placing the composite paste in the gap between the plates of a rheometer and with a shear rate of 4 $s^{-1}$. The composition takes on a Newtonian character with the addition of dispersant. The viscosity does not change even at a high shear rate.

Example 3

Photopolymerization of Dental Restoration Formulations 1, 2 and 3 (§2.2, 2.3 and 2.4 Above)

The formulations crosslink over a thickness of 3 mm in 40 of irradiation with an Optilux® Demetron lamp. The Vickers hardness measured after photocrosslinking is 50 for each of the three formulations. The flexural modulus and flexural strength measured in accordance with standard ISO4049 are 5 GPa and 80 MPa respectively.

Example 4

4.1 Preparation of a Formulation with Phosphate Dispersant (830 ppm)

Counter-Example 4

A triple-blade mixer is charged with slow stirring (<10 revolutions/minute) with 125 g of monomer (A) and 15 g of a solution of Solsperse® 36000, sold by AVECM, at a concentration of 4% in the monomer A. Mixing is carried out for 5 minutes. 18 g of photoinitiator system are added, containing 30% of photoinitiator P1 and 0.23% of photosensitizer based on chloropropoxythioxanthone CPTX. The ingredients are mixed at ambient temperature for 5 minutes.

Quartz ($SiO_2$>99%) with a particle size of 3.5 µm, sold by Schott, is added, in an amount of 378.5 g, and 45 g of ytterbium trifluoride are added. The mixture is mixed for approximately one hour at ambient temperature until a homogeneous fluid viscous mixture is obtained. 137 g of OX50 fumed silica are added gradually over 2 hours, by successive additions of 15 g. The mixture is stored in 5 g cartridges after filling in a climatized area at 25° C.

4.2 Preparation of a Formulation with Dispersant without Phosphate (830 ppm)

Example 4

The same operation as above is repeated, replacing the 15 g of Solsperse® 36000 solution by 15 g of Disperbyk® 164 0.4%, with an amine index of 20 mg of KOH/g of dispersant.

Observation is then carried out to ascertain how many months elapsed before the products, stored in cartridge form, undergo gelling.

The stored product with phosphate dispersant gels in 3 months at 25° C. After one year the product with dispersant with an amine index ≦100 mg of potassium hydroxide/g of dispersant is still useable and has not gelled. It crosslinks over 3 mm in less than 1 minute, with a flexural modulus of close to 10 GPa and a flexural strength of 80 MPa.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A dental composition useful for the production of dental prostheses and dental restoration materials, the dental composition comprising:
   (1) at least one compound which is reactive cationically and under activation;
   (2) at least one dental filler present in a proportion of at least 10% by weight relative to the total weight of the composition;
   (3) at least one organic polymer or copolymer dispersant having an amine index less than or equal to 100 mg of potassium hydroxide per gram of dispersant;
   (4) at least one cationic photoinitiator; and
   (5) optionally, at least one photosensitizer.

2. The dental composition as defined by claim 1, said at least one dispersant (3) having an acid index of less than 200 mg of potassium hydroxide per gram of dispersant.

3. The dental composition as defined by claim 1, said dental filler (2) comprising from 10 to 85% by weight thereof.

4. The dental composition as defined by claim 1, said at least one dispersant (3) comprising a polyurethane/acrylate copolymer, optionally in alkylammonium salt form.

5. The dental composition as defined by claim 1, said at least one dispersant (3) comprising from 50 ppm to 1% by weight thereof.

6. The dental composition as defined by claim 1, said at least one cationically reactive compound (1) being selected from the group consisting of monomers and/or (co)polymers of epoxies, vinyl ethers, oxetanes, spiroorthocarbonates, spiroorthoesters and combinations thereof.

7. The dental composition as defined by claim 1, said at least one cationically reactive compound (1) comprising at least one crosslinkable and/or polymerizable silicone oligomer or polymer which is liquid at ambient temperature or thermofusible at a temperature of less than 100° C. and which comprises:

at least one unit of formula (FS):

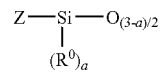

in which a=0, 1 or 2; the radicals $R^0$, which may be identical or different, are each an alkyl, cycloalkyl, aryl, vinyl, or alkoxy radical, or hydrogen; and the radicals Z, which may be identical or different, are each an organic substituent containing at least one reactive epoxy and/or alkenyl ether and/or oxetane and/or dioxolane and/or carbonate function; and at least two silicon atoms.

8. The dental composition as defined by claim 7, wherein in formula (FS), Z is an organic substituent Z1 containing at least one reactive epoxy and/or dioxolane function.

9. The dental composition as defined by claim 6, said at least one oligomer or polymer (1) further comprising reactive alkenyl ether, oxetane and/or carbonate functions Z2.

10. The dental composition as defined by claim 7, wherein in formula (FS), the reactive function or functions Z1 are selected from among the following radicals:

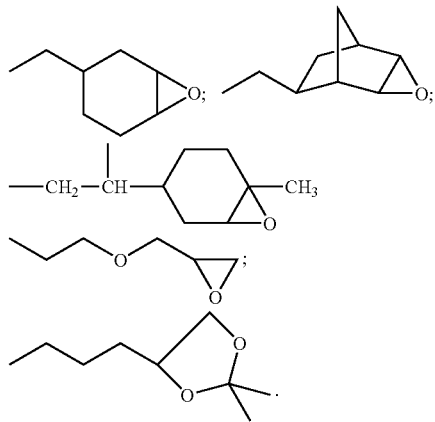

11. The dental composition as defined by claim 1, said at least one photoinitiator (4) comprising a borate photoinitiator selected from the group consisting of those of the formulae: the cationic borate moiety of which comprising:

(1) onium salts of formula (I):

$$[(R^1)_n\text{-A-}(R^2)_m]^+ \qquad (I)$$

in which formula:
A represents an element from Groups 15 to 17 of the Periodic Table;
$R^1$ represents a $C_6\text{-}C_{20}$ heterocyclic or carbocyclic aryl radical, with the proviso that said heterocyclic radical may contain nitrogen or sulfur as heteroelements,
$R^2$ represents $R^1$ or a $C_1\text{-}C_{30}$ linear or branched alkyl or alkenyl radical, the said radicals $R^1$ and $R^2$ being optionally substituted by a $C_1\text{-}C_{25}$ alkoxy, $C_1\text{-}C_{25}$ alkyl, nitro, chloro, bromo, cyano, carboxyl, ester or mercapto group,
$\underline{n}$ is an integer ranging from 1 to v+1, $\underline{v}$ being the valency of the element A,
and
$\underline{m}$ is an integer ranging from 0 to v−1 with $\underline{n+m=v+1}$;

(2) an oxoisothiochromanium salt;

(3) organometallic salts of formula (III):

$$(L^1L^2L^3M)^{+q} \qquad (III)$$

in which formula:
M represents a metal from Group 4 to 10 of the Periodic Table;
$L^1$ represents 1 ligand attached to the metal M by π electrons, the ligand being selected from $\eta^3$-alkyl, $\eta^5$-cyclopentadienyl and $\eta^7$-cycloheptatrienyl ligands and $\eta^6$-aromatic compounds selected from optionally substituted $\eta^6$-benzene ligands and compounds having 2 to 4 fused rings, each ring being capable of contributing to the valence shell of the metal M by 3 to 8π electrons,
$L^2$ represents one ligand attached to the metal M by π electrons, the ligand being selected from $\eta^7$-cycloheptatrienyl ligands and $\eta^6$-aromatic compounds selected from optionally substituted $\eta^6$-benzene ligands and compounds having 2 to 4 fused rings, each ring being capable of contributing to the valence shell of the metal M by 6 or 7π electrons,
$L^3$ represents from 0 to 3 identical or different ligands attached to the metal M by σ electrons and selected from CO and $NO_2^+$, the total electronic charge q of the complex to which $L^1$, $L^2$ and $L^3$ contribute and the ionic charge of the metal M being positive and equal to 1 or 2; and
the anionic borate moiety of which having the formula $[BX_aR_b]^-$, in which:
$\underline{a}$ and $\underline{b}$ are integers ranging from 0 to 3 for $\underline{a}$ and from 1 to 4 for $\underline{b}$, with $\underline{a+b=4}$,
the symbols X represent:
a halogen atom with $\underline{a}$=0 to 3, or
an OH function with a=0 to 2,
the symbols R, which may be identical or different, are each:
a phenyl radical substituted by at least one electron-withdrawing group and/or by at least 2 halogen atoms when the cationic moiety is an onium of an element from Groups 15 to 17 of the Periodic Table;
a phenyl radical substituted by at least one electron-withdrawing element or group;
an aryl radical containing at least two aromatic nuclei, optionally substituted by at least one electron-withdrawing element or group.

12. The dental composition as defined by claim 1, said at least one photoinitiator (4) being selected from the group consisting of:

$[(C_8H_{17})\text{—O-}\phi\text{-I-}\phi]^+,[B(C_6F_5)_4]^-$;
$[C_{12}H_{25}\text{-}\phi\text{-I-}\phi]^+,[B(C_6F_5)_4]^-$;
$[(C_8H_{17}\text{—O-}\phi)_2I)^+,[B(C_6F_5)_4]^-$;
$[(C_8H_{17})\text{—O-}\phi\text{-I-}\phi)]^+,[B(C_6F_5)_4]^-$;
$[(\phi)_2S\text{-}\phi\text{-O—}C_8H_{17}]^+,[B(C_6H_4CF_3)_4]^-$;
$[(C_{12}H_{25}\text{-}\phi)_2I]^+,[B(C_6F_5)_4]^-$;
$[CH_3\text{-}\phi\text{-I-}\phi\text{-CH}(CH_3)_2]^+,[B(C_6F_5)_4]^-$;
($\eta^5$-cyclopentadienyl)($\eta^6$-toluene)$Fe^+$,$[B(C_6F_5)_4]^-$;
($\eta^5$-cyclopentadienyl)($\eta^6$-methyl-1-naphthalene)$Fe^+$,$[B(C_6F_5)_4]^-$;
($\eta^5$-cyclopentadienyl)($\eta^6$-cumene)$Fe^+$,$[B(C_6F_5)_4]^-$;
$[(C_{12}H_{25}\text{-}\phi)_2I]^+,[B(C_6H_3(CF_3)_2)]^-$;
$[CH_3\text{-}\phi\text{-I-}\phi\text{-CH}_2CH(CH_3)_2]^+,[B(C_6F_5)_4]^-$; and
$[CH_3\text{-}\phi\text{-I-}\phi\text{-CH}_2CH(CH_3)_2]^+,[B(C_6H_3(CF_3)_2)_4]^-$.

13. The dental composition as defined by claim 1, comprising at least one aromatic hydrocarbon photosensitizer (5) containing one or more substituted or unsubstituted aromatic nuclei and having a residual absorption of light between 200 and 500 nm.

14. The dental composition as defined by claim 13, said at least one photosensitizer (5) being selected from the group consisting of:

4,4'-dimethoxybenzoin;
2,4-diethylthioxanthone;
2-ethylanthraquinone;
2-methylanthraquinone;
1,8-dihydroxyanthraquinone;
dibenzoyl peroxide;
2,2-dimethoxy-2-phenylacetophenone; benzoin;
2-hydroxy-2-methylpropiophenone; benzaldehyde;
4-(2-hydroxyethoxy)phenyl 2-hydroxy-2-methylpropyl ketone;
benzoylacetone;

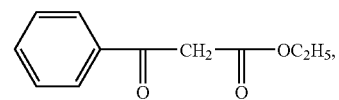

2-isopropylthioxanthone;
1-chloro-4-propoxythioxanthone;
4-isopropylthioxanthone;

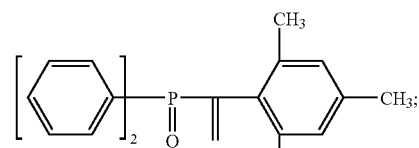

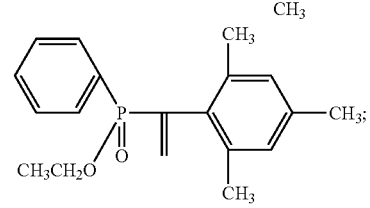

and mixtures thereof.

15. The dental composition as defined by claim 1, comprising at least one silicone oligomer and/or polymer (1) which comprises at least one silicone having one of the following average formulae:
a)
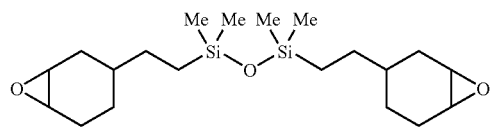
b)
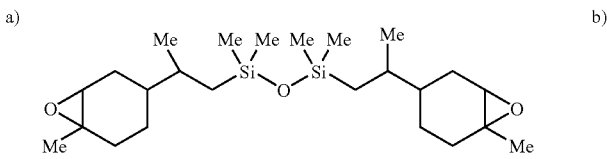
c)
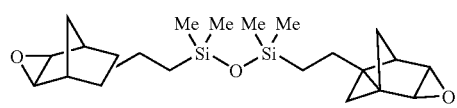
d)
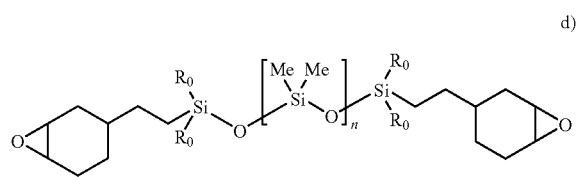
(n < 1000)
e)
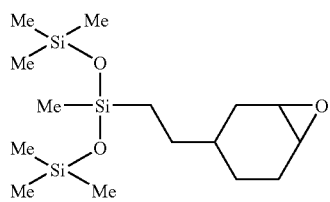
f)
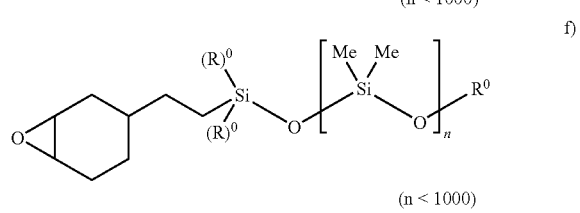
(n < 1000)
g)
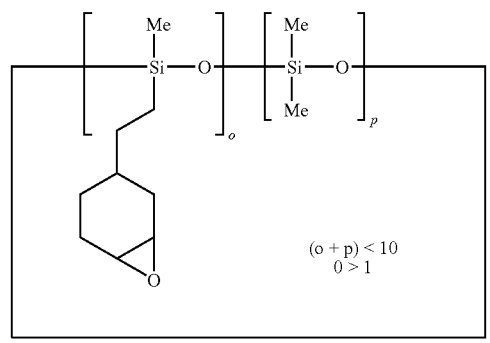
(o + p) < 10
o > 1
h)
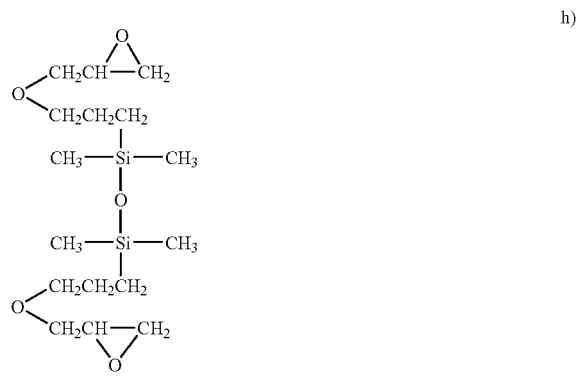
i)
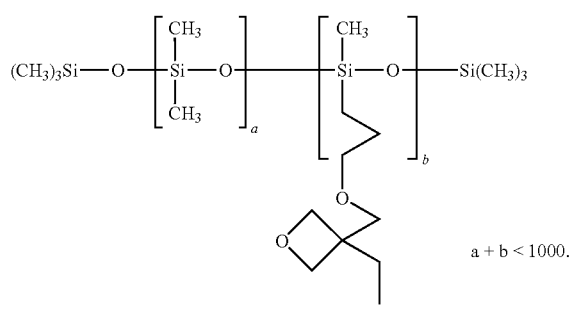
a + b < 1000.
j)
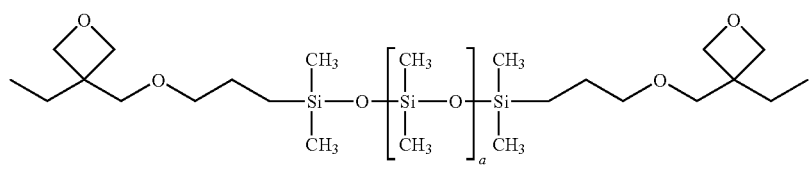
a < 1000.

-continued

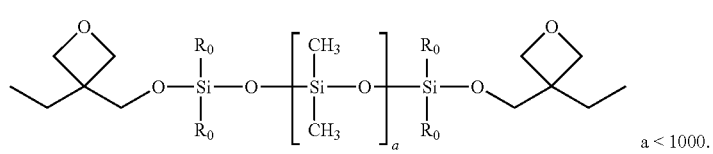

k)

a < 1000.

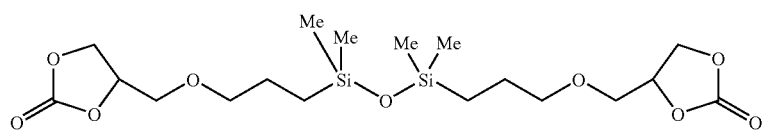

l)

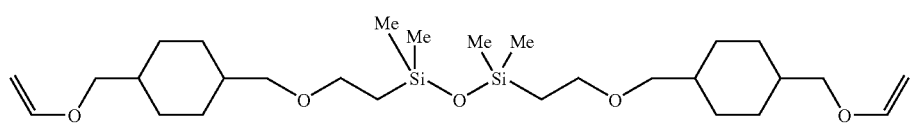

m)

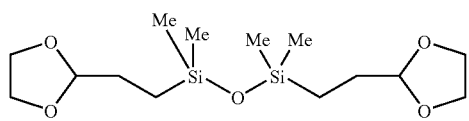

n)

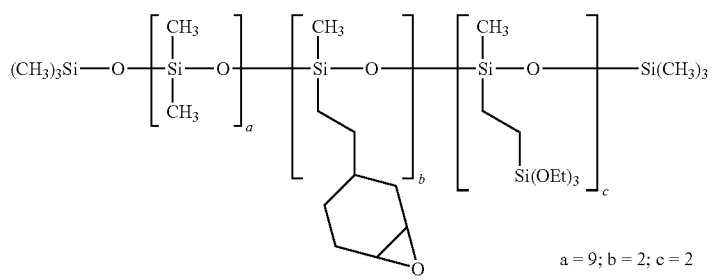

o)

a = 9; b = 2; c = 2

16. A dental prosthesis shaped from the dental composition as defined by claim 1.

17. A dental restoration material prepared from the dental composition as defined by claim 1.

18. The dental composition as defined by claim 1, comprising at least one compound (1) which is reactive cationically under actinic activation.

19. The dental composition as defined by claim 5, said at least one dispersant (3) comprising from 100 ppm to 5,000 ppm therein.

20. The dental composition as defined by claim 1, comprising (1) at least one UV- and cationically reactive oxirane-functionalized silicone.

* * * * *